(12) United States Patent
Chu

(10) Patent No.: US 7,560,075 B2
(45) Date of Patent: Jul. 14, 2009

(54) PLANAR REGISTRATION OF MULTI-WELL PLATE FROM WELL SIDE

(75) Inventor: Daniel Y. Chu, Hercules, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 242 days.

(21) Appl. No.: 11/339,087

(22) Filed: Jan. 24, 2006

(65) Prior Publication Data

US 2008/0199365 A1  Aug. 21, 2008

(51) Int. Cl.
*B01L 9/00* (2006.01)
(52) U.S. Cl. ............................ 422/104; 422/99; 422/130
(58) Field of Classification Search .................. 422/104, 422/130, 63, 99
See application file for complete search history.

(56) References Cited

U.S. PATENT DOCUMENTS

| 4,215,092 A * | 7/1980 | Suovaniemi et al. ...... 73/863.32 |
| 2001/0008615 A1 * | 7/2001 | Little et al. .................. 422/102 |

\* cited by examiner

*Primary Examiner*—Jill Warden
*Assistant Examiner*—Natalia Levkovich
(74) *Attorney, Agent, or Firm*—Townsend and Townsend and Crew LLP; Henry Heines

(57) ABSTRACT

A multi-well plate such as a microtiter plate is secured from its well side in a manner that corrects or compensates for any deviations of the plate base from a planar configuration. This is achieved by an apparatus that includes an array of posts with exposed tips that define a plane, a plurality of movable collets that, when appropriately actuated, seize the walls of selected wells, and a biasing means to urge the collets in a direction that forces the wells of the microtiter plate against the exposed tips of the posts.

13 Claims, 6 Drawing Sheets

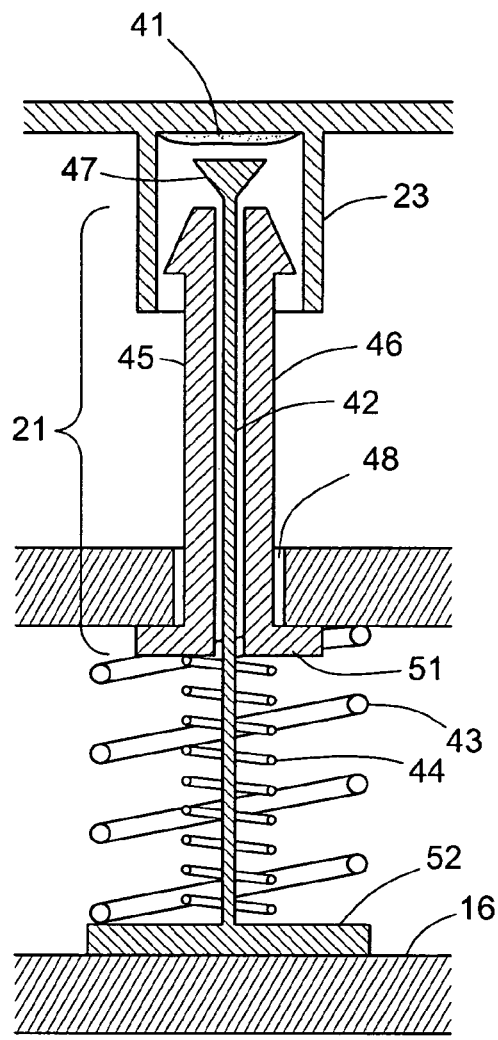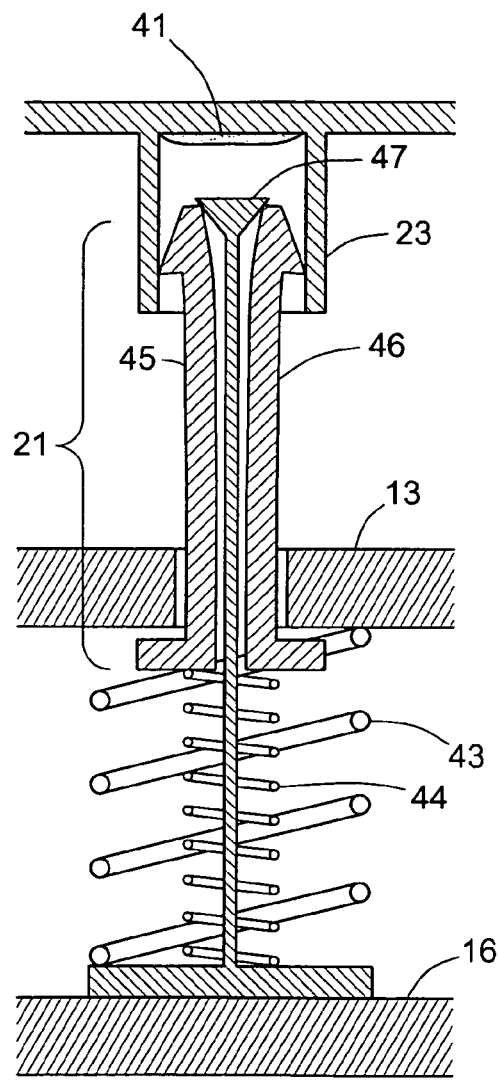
Fig. 5a
Fig. 5b

PLANAR REGISTRATION OF MULTI-WELL PLATE FROM WELL SIDE

BACKGROUND OF THE INVENTION

1. Field of the Invention

This invention resides in the field of laboratory equipment used in performing assays on a multitude of species or reaction media simultaneously in individual wells of a microtiter plate and multi-well plates in general that are designed for performing large numbers of small-volume assays simultaneously. In particular, this invention addresses matters arising when assays in these plates are read or monitored by optical scanning.

2. Description of the Prior Art

The standard microtiter plate with 96 wells in a 12×8 array and a spacing of 9 mm between wells is one example of the wide variety of multi-well plates used in performing automated chemical or biochemical assays for purposes such as screening or determining binding affinities, reactivities, or other characteristics of large numbers of species. Other multi-well plates contain as few as 24 wells or as many as 1536 wells, with various sizes in between. The species analyzed in these plates are often biological species such as proteins or nucleic acid fragments, but can also be small molecule libraries randomly prepared by chemical laboratories for purposes such as cheminformatics and bioinformatics, or more specifically, chemical or biological activity screening, gene function determination, and target validation.

Optical scanning is widely used for detection in these plates, since optical scanning can be performed by scanning heads that perform all of the detection functions and yet are small enough to focus on individual wells while rapidly traversing the entire well array. In addition, optical data from multiple wells is readily stored, quantified, and otherwise processed by automated instrumentation. To achieve high performance with large numbers of small-sized wells, the most effective optical scanning systems are those that utilize confocal optics with a depth of field that is on the order of a few millimeters or less. Since the height of the typical multi-well plate far exceeds this range, many multi-well plates are constructed with flat bottoms of glass or other transparent material so that scanning can be performed through the bottom of the plate. This is particularly effective when the solvents and other suspending media have been removed from the wells and the reaction products are deposited in a layer on the floor of each well. Accurate and uniform scanning however still requires that the plate be held in a secure position at a uniform and controlled distance from the travel plane of the scanning head. With the small distance, typically from about 1.0 mm to about 1.7 mm, that must be maintained between the surface of the glass and the scanning head, the plate cannot be grasped or secured from the rear, i.e., the scanning head side, since any such securement would interfere with the travel of the scanning head and any specialized fixtures that might be built into the plate bottom for this purpose would either do likewise or require that the plate be increased in length or width to accommodate such fixtures. Irregularities in the thickness of the transparent bottom will further interfere with the scanning accuracy.

SUMMARY OF THE INVENTION

These and other concerns and limitations are addressed by the present invention, which resides in apparatus for supporting a multi-well plate from the well side of the plate by a combination of posts with exposed tips or ends that support the transparent plate at the overturned base of the multi-well plate, and two or more collets to grasp the wells by the well walls. The exposed tips of the posts collectively define a plane in which the floor of each well will reside (i.e., to which the well floors will be registered) and the collets independently force the wells and hence the plate against the posts so that the multi-well plate is pressed against the tip of each post. To fix the tips of the posts within a common plane, the posts are mounted to a post support common to all of the posts. When reaction media residues are deposited on the floors of the wells, the location of each residue is thus fixed within the plane defined by the post tips and any irregularities in the multi-well plate construction that might produce a deviation in the depths of the wells or in the thickness or flatness of the transparent base of the plate are compensated for or corrected, with the result that the residues all reside in the plane defined by the heights of the posts.

The apparatus of this invention is designed to grasp a multi-well plate from the well side of the plate, and can do so with the plate in an upright position with the wells facing upward and the transparent base at the bottom, or in an inverted or overturned position with the wells facing downward and the transparent base at the top. With the plate in an upright position, the posts of the apparatus will extend downward, the apparatus will force the plate upwards against the post tips, and scanning will be performed from underneath the multi-well plate. With the plate in an inverted position, the posts will extend upward with the multi-well plate resting on the post tips for scanning from above while the apparatus forces the plate downward against the post tips.

The collets traverse the post support so that each collet can grasp a well of the multi-well plate. Associated with each collet is an actuator that manipulates the collet between a grasping condition and a released condition. In the grasping condition, the collet and well are joined such that the collet and well move as a unit, while in the released condition, the collet is free to move relative to the well. In certain embodiments, the collet is large enough to encircle the well and seize the external wall surfaces of the well, while in other embodiments, the collet is small enough to extend into the well interior and seize the well by its internal wall surfaces. In still further embodiments, the collet is sized to fit between adjacent wells, pressing against the external wall surfaces of two or more neighboring wells, or against webs connecting the walls of adjacent wells. In all of these embodiments, seizing of the well is thus achieved by either contraction or expansion of the collet, depending on whether the collet encircles the well or extends into the well interior. Likewise, release of the well from the collet is achieved by expansion if the collet encircles the well and by contraction if the collet extends into the well. While the movement of each collet between expanded and contracted conditions is controlled by the actuator, each collet is preferably resilient so that when relaxed the collet assumes one of the two conditions and when under tension by the actuator the collet is forced into the other of the two conditions. Thus, if the collet, when not under tension by the actuator, assumes the contracted position, the actuator will cause the collet to expand, and likewise, if the collet is expanded when not under tension by the actuator, the actuator will cause the collet to contract. In cases where the relaxed condition is a contracted condition, the actuator can for example be a rod that extends into the interior of the collet and has an expanded segment that forces the collet sections apart when the rod is moved to a certain position within the collet. In cases where the relaxed condition is an expanded condition, the actuator can be a sleeve encircling the collet and allowing the collet to expand only when the sleeve is retracted. Other configurations will be readily apparent to those skilled in the art.

For resilient collets, therefore, each actuator is operable between an engaged position in which each actuator applies tension to its associated collet and a disengaged position in which the tension is released. The actuators can be independently operable, but are preferably operable as a unit by a single knob, lever, switch, wheel, cam, or other implement that engages or disengages all actuators in a single motion, preferably an implement that can be manipulated manually by the user.

Each collet, when seizing a well, forces the well and hence the portion of the multi-well plate in the vicinity of the well against the post or posts nearest to the collet, and the force applied by each collet is independent of the force applied by all other collets. Regardless therefore of how many posts, and which posts, are in full contact with the multi-well plate, any gap that exists between any remaining post and the plate will be closed by the force exerted by a collet or collets in proximity to the remaining post. This is preferably achieved by securing the posts to a fixed support plate while the collets and actuators are not secured to the support plate but instead are free to move relative to the support plate, while independent tension is applied to each collet and actuator pair. Independent tension can for example be supplied by a separate spring or equivalent tensioning member for each collet and actuator pair, the spring located on the side of the support plate opposite the posts to force the collet, and the well seized by the collet, toward the plate. In certain embodiments, additional springs or tensioning members are included to maintain the relative positions of the collet and actuator.

As noted above, the tips of the posts define the plane against which the multi-well plate is registered. To accomplish this, the posts are arranged in a non-linear array, and at least three posts, preferably at least four, are included. The posts can be arranged such that the tips abut the plate either within the interiors of wells or at sites outside the wells. To direct the registration to the wells themselves, the posts are preferably aligned with individual wells. To minimize interference with the scanning of the species within the wells, the posts are preferably hollow or have cup-shaped ends. The diameters of the hollow posts or cup-shaped ends can be larger or smaller than those of individual wells. If larger, the posts will encircle, i.e., fit over, the wells and if smaller, the posts will fit inside individual wells, preferably contacting only the periphery of the well floor, avoiding contact with the center of the well.

BRIEF DESCRIPTION OF THE DRAWINGS

FIGS. 5a and 5b are cross sections of a collet of the apparatus of the preceding FIGS. and components associated with the collet, FIG. 5a showing the collet in a relaxed, non-seizing condition, and FIG. 5b showing the collet in an expanded, seizing condition.

FIGS. 6b and 6c show the component in a lowered position, and FIG. 6d shows the component in a raised position.

DETAILED DESCRIPTION OF THE INVENTION AND PARTICULAR EMBODIMENTS

Figure 1:
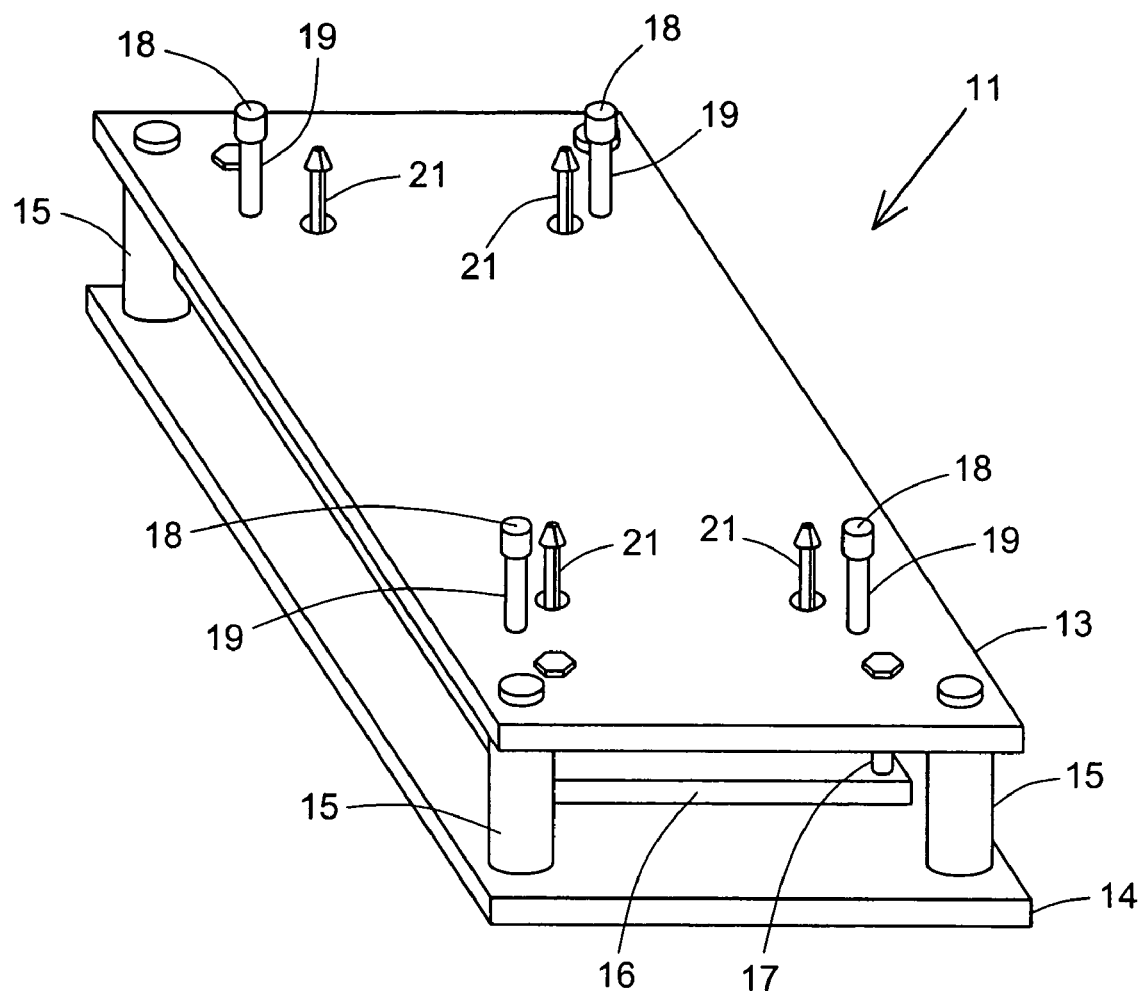
FIG. 1 is a perspective view of an apparatus in accordance with the present invention.

While the features defining this invention are capable of implementation in a variety of constructions, the invention as a whole will be best understood by a detailed examination of a specific embodiment. One such embodiment is shown in the drawings.

Figure 2:
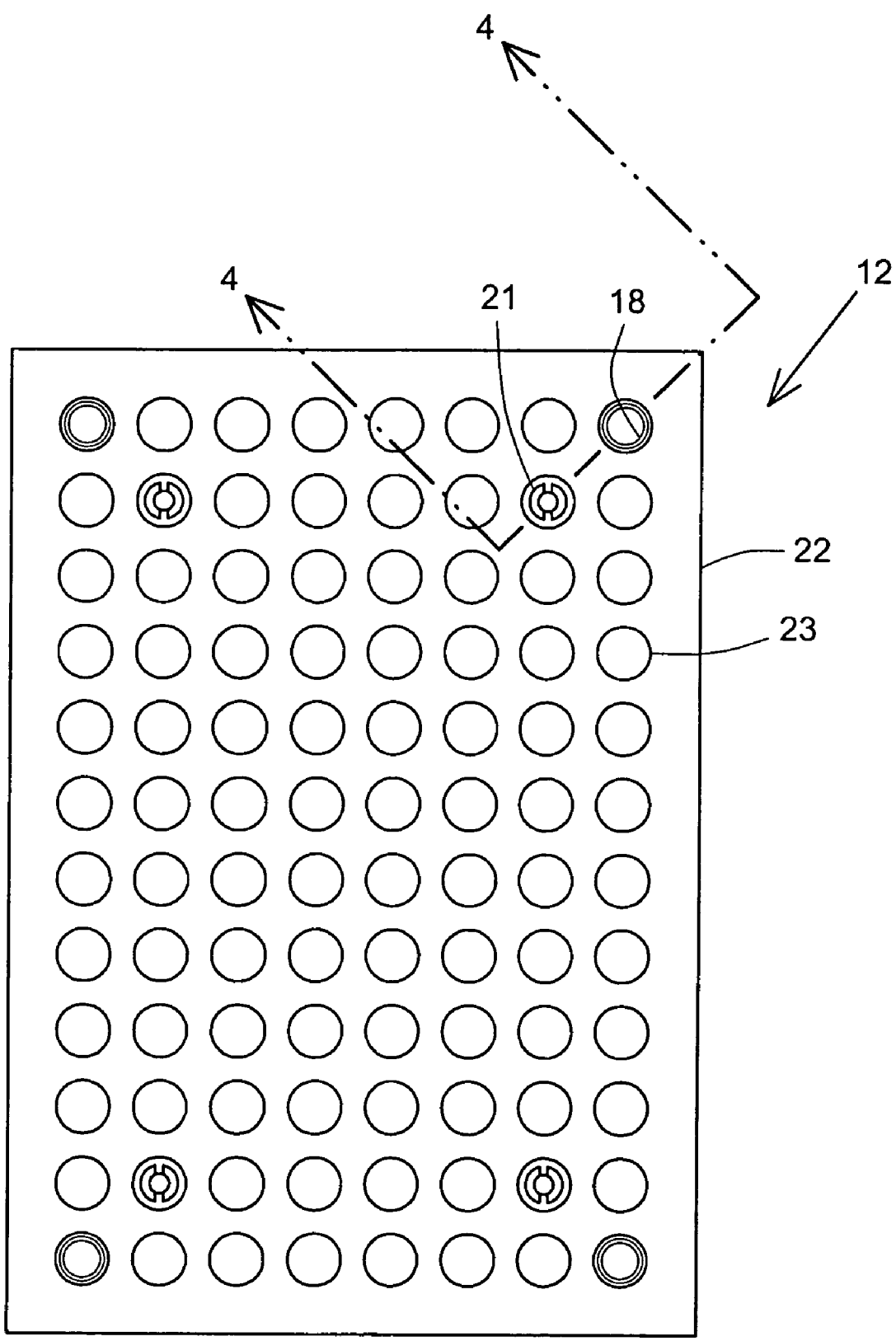
FIG. 2 is a plan view of an inverted microtiter plate and the components of the apparatus of FIG. 1 that contact the microtiter plate when in use.

FIG. 1 shows, in perspective, a unit 11 designed to support an inverted microtiter plate in the manner of the invention to maintain the microtiter plate in planar registration. FIG. 2 shows the inverted microtiter plate 12 itself in a plan view. The support unit 11 includes three rectangular plates, of which two are immovable upper and lower plates 13, 14 and the third is a middle plate 16 positioned between the upper and lower plates. The upper and lower plates 13, 14 are approximately equal to each other in length and width and are rigidly secured to each other (and hence referred to herein as "fixed") in a parallel relation by four spacers 15, one spacer at each of the four corners of each plate. The movable plate 16 fits between the upper and lower plates in a manner that allows the movable plate to move without interference from the spacers. This is accomplished in the embodiment shown in FIG. 1 by using a movable plate that is smaller in width and length than the fixed plates and that fits inside the area bordered by the spacers 15. When the upper and lower plates 13, 14 are arranged horizontally, the movable plate 16 is capable of vertical movement, perpendicular to the upper and lower plates 13, 14. The movable plate is prevented from lateral movement and from tipping relative to the fixed plates by four guide posts, of which only one 17 is visible in FIG. 1. Each guide post 17 is secured to the upper plate 13 and extends downward, loosely passing through an aperture in the movable plate 16 to limit the movement of the movable plate to the vertical direction.

The plane to which the microtiter plate will be registered is defined by the tips 18 (i.e., the upper extremities) of four posts 19 that are rigidly mounted to the upper plate 13. The posts 19 are constructed so that the tips 18 are coplanar. Four collets 21 are shown as well, each collet extending through the upper plate 13 and movable relative to all three plates. The manner in which the collets 21 are supported is shown in the succeeding FIGS. and described below.

As noted above, the embodiment of FIG. 1 has four posts 19 and four collets 21, both arranged in rectangular arrays. Neither these numbers nor the geometrical arrangements are critical to the invention, and both can vary. To define a plane for planar registration of the microtiter plate, the posts 19 must be at least three in number and arranged in a non-linear array. A minimum of four posts is preferred, and a rectangular array is likewise preferred for its convenience and stability and its ability to flatten a warped microtiter plate. The collets 21, by contrast, are not intended to define a plane, and hence are not subject to the requirement of a non-linear array. To perform their function most effectively, however, the collets are equal in number to the posts and are preferably positioned such that one collet is in close proximity to each post. Accordingly, for a microtiter plate with wells arranged in a rectangular array, four posts 19 are preferred in a rectangular array that corresponds to the locations of the wells at each of the four corners of the microtiter plate, and four collets 21 positioned in close proximity to the posts 19 are likewise preferred. For large microtiter plates, additional control and stability can be afforded by including additional posts positioned inside the rectangle defined by the four corners, and including a corresponding number of additional collets. For any size microtiter plate, the number of collets is preferably equal to the number of posts. Regardless of the numbers of posts and collets, the tips of all posts will reside in the same plane.

The spacing of the posts 19 and collets 21 relative to the microtiter plate is illustrated in FIG. 2, which presents the microtiter plate in a view from the bottom surface of its base plate 22. The wells are arranged in the standard 8×12 rectangular array, although it is emphasized that this is an illustration only—the size of the plate and the number and arrangement of wells in the plate can vary widely. The support unit is positioned beneath the microtiter plate, below the plane of the FIG., and only the tips 18 of the support posts and the collets 21 are shown. Since the base plate 22 is glass or other transparent material, the outlines of the individual wells 23, the tips 18 of the support posts, and the upper ends of the collets 21, are all visible through the base plate. In the arrangement shown, the four tips 18 of the support posts engage the wells that occupy the four corners of the rectangular array, and the four collets 21 engage wells at the four corners of the smaller rectangle that lies within the rectangle formed by the posts and whose corners are as close a possible to those of the larger rectangle defined by the post tips 18.

Figure 3:
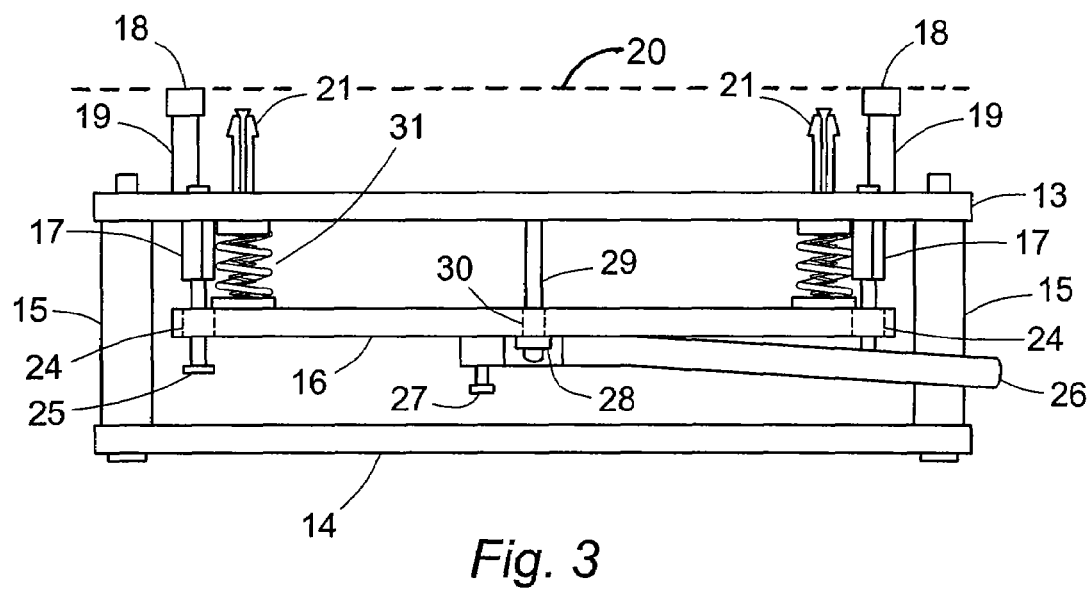
FIG. 3 is a side view of the apparatus of FIG. 1.

FIG. 3 is a side view of the support unit. This view shows the posts 19 and the post tips 18, and the plane 20 in which the post tips reside. Also shown are components of the mechanism for movement of the movable plate 16 and for limiting this movement to the vertical direction. As noted above, the movement of the plate is limited by guide posts 17 that pass through apertures in the plate, shown in dashed lines 24, the apertures having diameters slightly larger than the guide posts to allow movement of the plate. Each guide post 17 has a flange 25 at its lower extremity to serve as a stop to limit the downward motion of the plate. The range of downward motion can also be limited by the bar 26 that controls the vertical position of the plate 16. The bar 26 is pivotally mounted to the plate by a pivot connection 27 that allows the bar to pivot approximately parallel to the plate. The bar 26 engages the flanged end 28 of a peg 29 that is mounted to, and extends downward from, the upper plate 13. The peg 29 is rigidly affixed to the upper plate 13 and the shaft of the peg passes through an aperture in the movable plate 16. The aperture is shown in dashed lines 30 and has a diameter that is larger than the shaft, allowing the movable plate 16 to rise and fall relative to the peg. The bar 26 and peg 29 are shown in greater detail in FIGS. 6a, 6b, and 6c which are described below.

Further details shown in FIG. 3 include a combination of compression springs 31 associated with each collet to control the position and force on the collet in conjunction with the position of the movable plate 16. These springs, as well as the collets and their components are shown in FIGS. 4, 5a, and 5b and described below.

Figure 4:
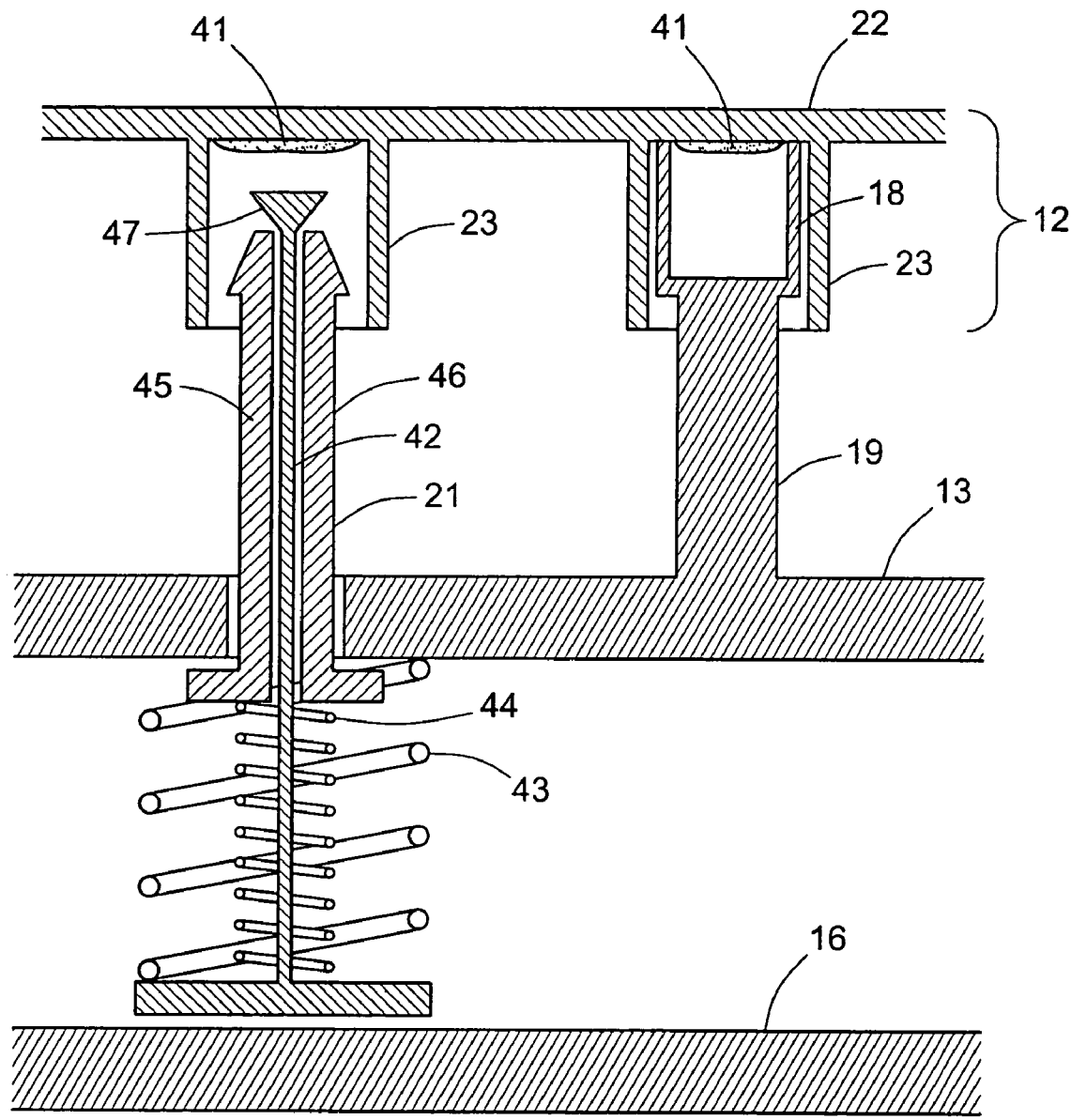
FIG. 4 is a cross section of the apparatus of FIG. 1 and the microtiter plate of FIG. 2, taken along the line 4-4 of FIG. 2.

FIG. 4 is a cross section taken along the line 4-4 of FIG. 2, showing the microtiter plate 12 and the fixed upper plate 13 and movable plate 16 of the support unit 11. As in FIG. 2, the microtiter plate 12 in FIG. 4 is inverted such that the wells open downward. Prior to inversion of the microtiter plate, solvent has been removed from the reaction media in each well, leaving the reaction species as a solid residue 41 deposited on the floor of each well. With the microtiter plate inverted as shown, the scanning head passes over the inverted base plate 22 with only the base plate 22 separating the scanning head from the residue to be scanned.

The support post 19 in this particular embodiment is a shaft terminating in a hollow or cup-shaped end 18 (referred to elsewhere herein as the "tip" of the post). The hollow end 18 fits loosely inside the inverted well 23 for easy placement of the microtiter plate on the posts and easy removal after scanning. The hollow shape minimizes contact between the tip and the residue 41 to be scanned and minimizes any interference of the post with the optical signal generated by the scanning head, particularly when the scan head is focused on the center of the well floor.

The collet 21 and associated parts include the collet itself 21, an actuator 42, and two compression springs 43, 44, which together constitute the spring combination 31 of FIG. 3. Neither the collet, the actuator, nor the springs are affixed to any of the three plates. The collet 21 is split or slotted at its upper end, although for enhanced visibility the Figure shows the collet to be split along its entire length. The split divides the collet into two or more longitudinal fingers 45, 46 that can be spread apart when a radially outward force is applied from inside the collet. The fingers are sufficiently resilient however to return to the condition shown in FIG. 3 when the force is removed. The force is supplied by the actuator 42, which is a rod passing through the center of the collet. The rod has a wedge-shaped segment, which in this particular structure is a truncated cone 47 at the terminus of the rod.

The function of this wedge-shaped segment and the operation of the actuator are illustrated in FIGS. 5a and 5b. A downward axial movement of the actuator rod from the condition depicted in FIG. 5a to the condition depicted in FIG. 5b draws the wedge 47 between into the interior of the collet, forcing the two halves 45, 46 of the collet apart, while an upward movement to return to the condition of FIG. 5a raises the wedge and allows the two halves to draw back together. FIG. 5a thus represents the relaxed condition of the collet 21. In this condition, the collet is not in contact with, and does not exert a seizing force on, the internal walls of the well 23. In the expanded condition of FIG. 5b, the two halves 45, 46 of the collet press against the internal walls of the well, seizing the well to the extent that a downward force on the collet draws the well and the adjacent portions of the microtiter plate downward with the collet. The collet 21, which is not secured to any of the other parts, passes through an aperture 48 in the fixed plate 13, and the collet terminates at its lower end in a flange 51 which limits the upward movement of the collet and prevents the exposed tip of the collect from contacting the residue 41 at the floor of the well. The actuator 42 is likewise not secured to any of the other parts, and likewise terminates at its lower end in a flange 52. The actuator flange 52 rests on the movable plate 16 and is forced upward when the actuator plate is forced upward.

The spring combination consists of two springs of different degrees of stiffness, both operating under compression. The outer spring 43 is stronger, i.e., has a larger spring constant, than the inner spring 44. The outer spring 43 is compressed between the flange 52 at the base of the actuator 42 and the undersurface of the movable plate 13. Thus, when the movable plate 16 is lowered, the outer spring 43 presses against the lower flange 52 of the actuator, forcing the actuator down and the wedge 47 of the actuator into the opening between the two halves 45, 46 of the collet. Since the outer spring 43 does not contact the collet 21, the outer spring exerts its force only on the actuator 42 and not on the collet. The inner spring 44 prevents the collet from being lowered the same distance as the actuator by pressing the collet upward. Once the well 23 is seized by the collet 21 as in FIG. 5b, the collet 21 will continue to draw the well 23 down until the downward travel of the well is stopped by the tip of a support post. The collets thus function independently in the sense that once all collets are in an expanded condition with each collet seizing a separate well, each outer spring 43 continues to exert a downward force on the collet at its center until the well seized by the collet abuts the nearest post. Stoppage of the downward travel of one well does not result in stoppage of the downward travel of another well if there remains a gap between an adjacent well and the post extending inside that well.

Figure 6A:
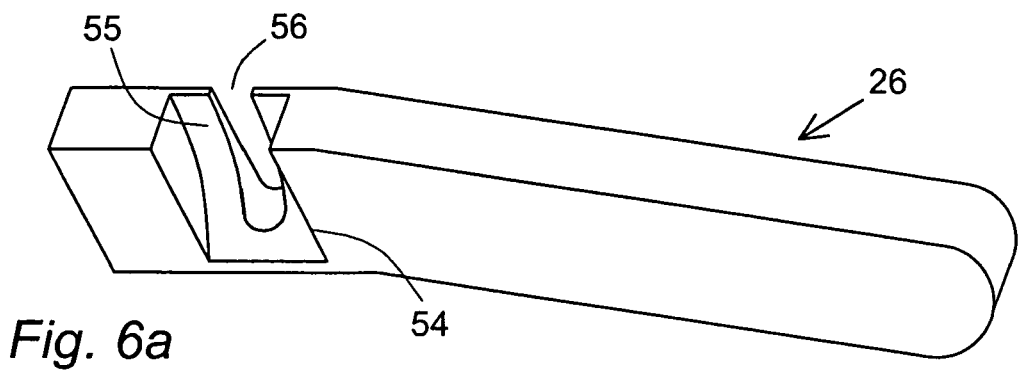
FIGS. 6a, 6b, 6c, and 6d are a perspective view, an end view, and two cross section views, respectively, of one component of the apparatus the preceding FIGS., FIGS. 6c and 6d taken along the line c-c of FIG. 6b.
Figure 6B:
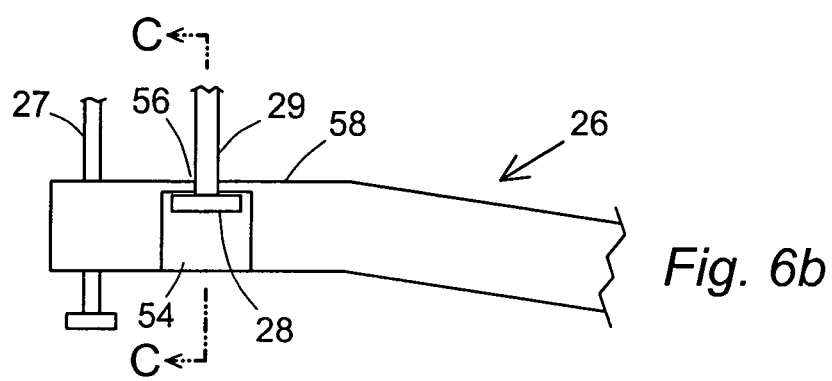
Figure 6C:
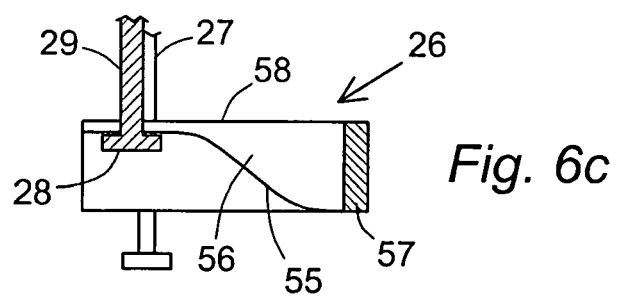
Figure 6D:
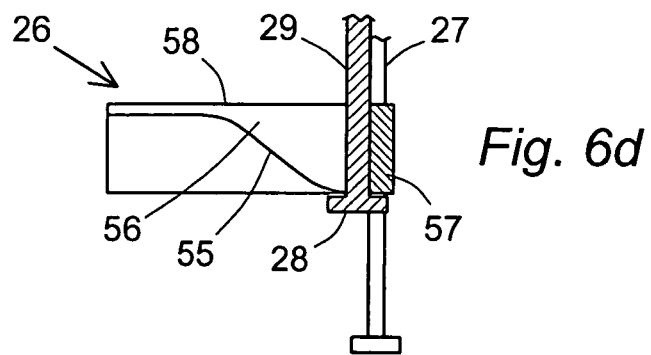

The bar mechanism controlling the position of the movable plate 16 is shown in FIGS. 6*a*, 6*b*, 6*c*, and 6*d*. The perspective view of FIG. 6*a* shows that the bar 26 has an inverted trough 54 with a sloped ceiling 55 and a slot 56 in the ceiling. In the side view of FIG. 6*b*, the pivot connection 27 is visible at one end of the bar 26 and the peg 29 and its flanged end 28 are also visible. The trough 54 receives the flanged end 28 of the peg, while the slot 56 allows passage of the peg shaft. The cross sections of FIGS. 6*c* and 6*d*, taken along the line c-c of FIG. 6*b*, show that the sloped ceiling 55 in profile and the end wall 57 that truncates the slot 56. End walls may be included at both ends as a further option. FIGS. 6*c* and 6*d* show the bar in two positions, respectively, representing the two extremes of its pivoting travel. The sloped ceiling 55 of the trough causes the bar to rise as the bar pivots into the position shown in FIG. 6*d*. Since the upper surface 58 of the bar is in contact with the lower surface of the movable plate, and the rise of the bar 26 upon pivoting to this position causes the movable plate to rise with the bar.

While the foregoing description describes various alternatives to the components shown in the Figures, still further alternatives still within the scope of the invention can be introduced. The upper and lower fixed plates and the movable plate, for example, can be replaced by open frames or grids that likewise support the components that are affixed to them and that contain openings for the components that extend through them and that are movable relative to them. Alternatives to the guide posts 17 shown in FIGS. 2 and 3 are frames or brackets positioned along the edges or at the corners of the movable plate without passing through the plate. Alternatives to the compression springs are any other individual biasing members for the collets, such as tension clips, resilient foams, or air-filled bladders. Alternatives for the bar that raises and lowers the movable plate are knobs, pressurized fluids, and motorized cams. Still further variations and embodiments, all within the scope of this invention, will be apparent to those who are skilled in the art of microtiter plate usage and processing equipment and have studied the drawings and descriptions offered above.

What is claimed is:

1. Apparatus for registration of the wells of a multi-well reaction plate relative to a selected plane, said apparatus comprising:

a plurality of posts mounted to a common post support in a non-linear array, each said post terminating in an exposed tip and all of said exposed tips residing within said selected plane;

a plurality of collets traversing said post support, each said collet engaged by an actuator and independently movable;

a biasing member for each collet, urging each said collet away from said selected plane; and actuating means for moving each said actuator between a position causing expansion of said collet and a position causing contraction of said collet.

2. The apparatus of claim 1 wherein said actuating means comprises a single means for moving all of said actuators simultaneously.

3. The apparatus of claim 1 wherein said actuating means comprises a single manually operated device for moving all of said actuators simultaneously.

4. The apparatus of claim 1 wherein said actuators are rods positioned inside said collets.

5. The apparatus of claim 1 in which each of said collets is resilient and assumes a contracted condition when relaxed and an expanded condition when under tension by said actuator.

6. The apparatus of claim 4 wherein each of said rods comprises a segment having a wedge-shaped profile causing expansion of said collet when said segment is retracted inside said collet.

7. The apparatus of claim 1 wherein said common post support is a support plate with said posts extending to one side thereof, and each of said biasing members urges a collet toward said support plate.

8. The apparatus of claim 1 wherein said biasing members comprise compression springs.

9. The apparatus of claim 1 wherein said actuators are rods positioned inside said collets, said apparatus further comprises a movable plate that is movable relative to said common post support and that abuts said rods, and said biasing members are compression springs compressed between said common post support and said movable plate.

10. The apparatus of claim 9 wherein said actuating means comprises a single manually operated device arranged to position said movable plate relative to said support plate.

11. The apparatus of claim 1 wherein said plurality of posts consists of at least four said posts arranged in a rectangular array.

12. The apparatus of claim 1 wherein said plurality of posts consists of at least four said posts arranged in a rectangular array, and said plurality of collets consists of at least four said collets arranged in a rectangular array.

13. The apparatus of claim 1 wherein said common post support is a support plate with said posts extending to one side thereof, each of said biasing members comprises first and second compression springs for each collet, said first compression spring engaging said actuator and said support plate, and said second compression spring engaging said actuator and said collet.

\* \* \* \* \*